United States Patent [19]
Yoshida

[11] Patent Number: 5,268,968
[45] Date of Patent: Dec. 7, 1993

[54] DEFECT JUDGEMENT METHOD

[75] Inventor: Hajime Yoshida, Tokyo, Japan

[73] Assignee: Hajime Industries, Tokyo, Japan

[21] Appl. No.: 823,316

[22] Filed: Jan. 21, 1992

[30] Foreign Application Priority Data

Jan. 24, 1991 [JP]  Japan .................................. 3-24124

[51] Int. Cl.⁵ ............................................. G06K 9/00
[52] U.S. Cl. ........................................ 382/8; 358/106; 358/107; 364/564
[58] Field of Search .................... 382/8, 1, 19, 23, 25; 358/106, 107; 364/560, 564

[56] References Cited

U.S. PATENT DOCUMENTS 4,700,224 10/1987 Miyasaka et al. ........................ 382/8
5,046,115 9/1991 Maruyama et al. .................. 358/106

Primary Examiner—Michael T. Razavi
Assistant Examiner—Yon J. Couso
Attorney, Agent, or Firm—Bauer & Schaffer

[57] ABSTRACT

A video image is obtained of an object and divided into a matrix of horizontal and vertical zones. The matrix is scanned sequentially and those zones determined to have defects stored. The position of each of the stored zones are determined by the distance horizontally and vertically from a base comprising the zone indicated preceding in the scan.

5 Claims, 2 Drawing Sheets

DEFECT JUDGEMENT METHOD

BACKGROUND OF THE INVENTION

1. Field of the Invention

The present invention relates generally to defect judgement methods of industrial products at the production processes and, more particularly, is directed to a defect judgement method for industrial products in its production line that utilizes a video camera and a computer or the like.

2. Description of the Prior Art

Defect detection methods are conventionally practiced in which a light is irradiated on an inspected object, a video camera picks up the image of the inspected object based on its passed or reflected light, and the image signal from the video camera is processed by an electronic processor such as a computer or the like which makes the judgement of the object.

Further, upon making the judgement as to whether the defect should be detected or not, methods involving means that a certain threshold value is setup against the image signal and that such a portion that responds to an image signal that exceeds the above threshold value is judged as a defect, have been mainly employed.

Generally, the shape of the flaws or the like that are to be detected as defects are extensively varied, for instance, some that contain severe notches or unevenness at the circumference, or a grouping of multiple small variant portions that look like a single flaw, etc. Accordingly, by the defect judgement methods that are conventionally practiced by setting up a mere threshold value against the image signal to judge anything exceeding such value as a defect, it is extremely difficult to determine the judgement basis as whether it should be a defect or not against flaws that contain such shape variations. For instance, a flaw that contains at its central portion a narrow crevice that visually appears as two flaws on micrographic basis shall be judged as one flaw by the conventional methods to an extent that an accurate judgement of defects was impossible.

OBJECTS AND SUMMARY OF THE INVENTION

In view of the above problems in the conventional methods, it is object of the present invention to provide a defect judgement method which can obviate the shortcomming encountered with the prior art in order to avail a method by which easy and accurate judgements are conducted by setups of judgement basis against flaw shapes or flaw sizes when defects with multiple variations are to be detected.

According to an aspect of the present invention, there is provided a defect judgement method in which an image of an inspected object is picked up by a video camera, an area formed of an image signal from said video camera is divisioned into horizontal and vertical lattice like zones, and a judgement as a defect of said inspected object is made by detecting brightness of each of said divisioned zones, which comprises steps of:

a) storing a position of one of said zones on said area which is detected as a defect at first upon scanning a picture screen of said video camera as a first base position;

b) measuring vertical and horizontal distances of a zone on said area which is detected as a defect at second based upon said first base position;

c) selecting and storing a position of said second zone as a second base position when said horizontal and vertical distances are within a preset distance;

d) measuring horizontal and vertical distances of a zone on said area which is detected as a defect at third based on said second base position;

e) selecting and storing a position of said third zone when said vertical and horizontal distances of said third zone are within a preset distance as a third base position; and f) judging a size of the defect based upon maximum distance in vertical and horizontal distances of a plurality of zones stored.

BRIEF DESCRIPTION OF THE DRAWINGS

A better understanding of the objects, features and advantages of the invention can be gained from a consideration of the following detailed description of a preferred embodiment thereof, in conjunction with figures of the accompanying drawings, wherein.

DESCRIPTION OF THE PREFERRED EMBODIMENT

One embodiment of the defect judgement method according to the present invention shall be explained with reference to the drawings hereunder.

Figure 1:
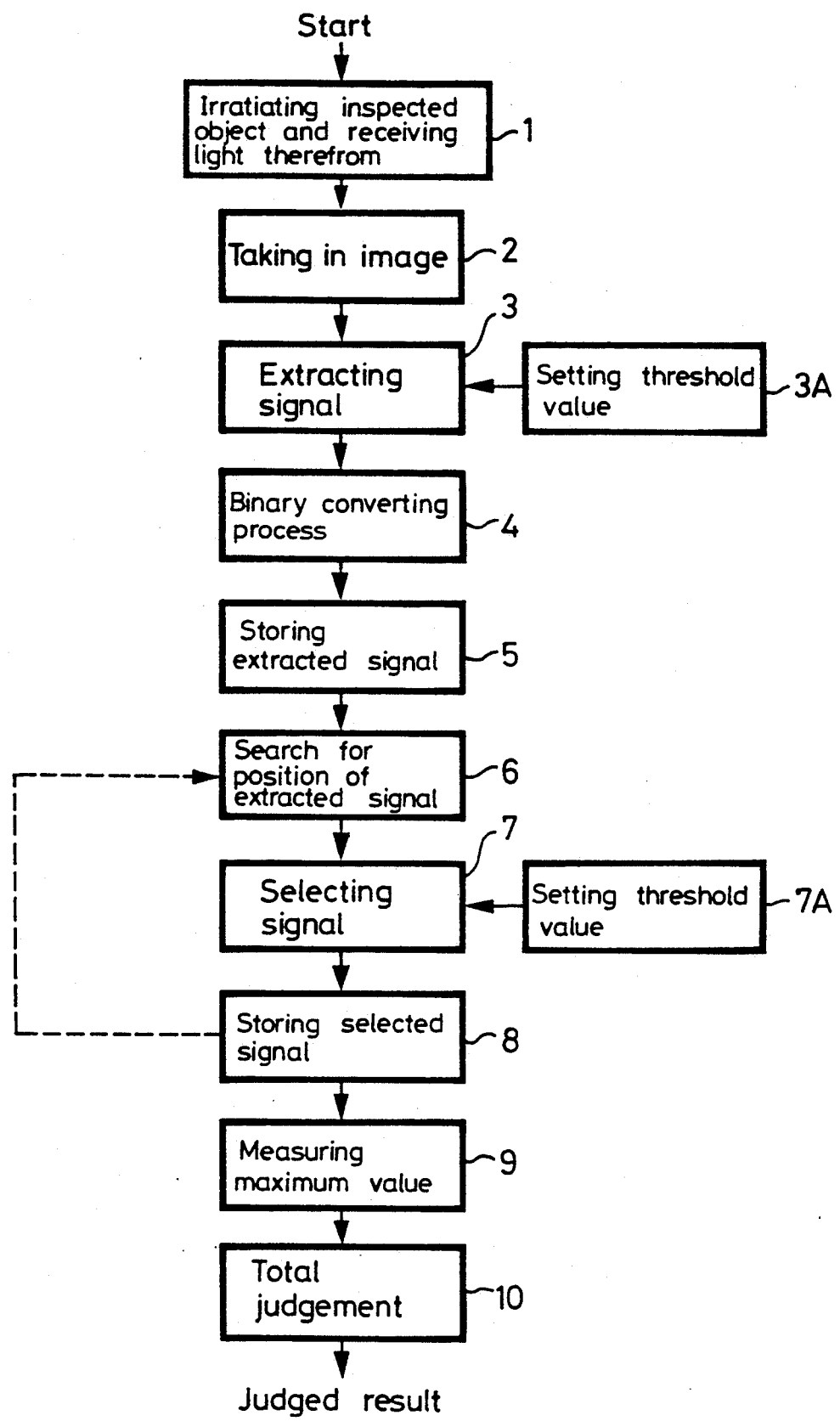
FIG. 1 is a function explanatory diagram of an example of the present invention.
Figures 2, 3:
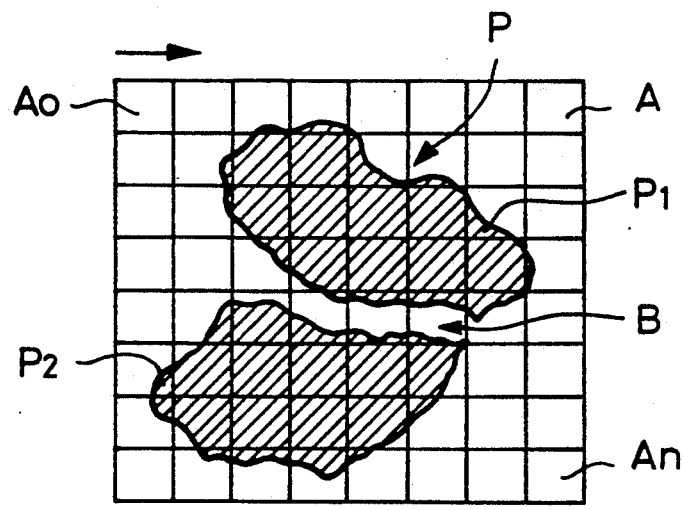
FIG. 2 is a schematic diagram to explain a defect shape.
FIG. 3 is an explanatory diagram that shows the vertical and horizontal distances of defect portions against a base position.

FIG. 1 shows the electronic processing flow of an electronic processor (not shown) of the present invention. FIG. 2 shows the shape of a flow P that is set up for explanation conveniences. For instance, when a video camera (not shown) that uses a solid state photosensing elements is employed, a part of the image that is obtained by picking up the flow P is magnified and is shown as overlapping on a lattice structured picture screen A of the video camera. Actually, the size of the pixels forming the screen A of the video camera is minute, but for a purpose of explanation, the size of the picture screen A is mocked up to an exaggerated large size. The processing method of the electronic processor that judges this flaw P as picked up by the video camera to be a flaw that should be a defect shall be explained hereunder.

FIG. 3 shows the pixels of a portion of the image screen A in lattice condition, whereas the pixels that are shown in thick lines from (1) to (20), illustrate that the portions corresponding to flaw P on FIG. 2 are extracted. On the assumption that there exists a narrow crevice B on the flow P shown on FIG. 2, there also is a gap C on the portion of the flaw as shown on the latticed pixels of FIG. 3.

In the electronic processing method at the inspection system so as to detect a flaw, the image signal obtained from the video camera is sliced by a predetermined threshold value to thereby extract the signal corresponding to flaw and the signal thus extracted is converted into a binary signal in order to memorize the same in a memory (not shown) which is known to be the general detection processing. Needless to say, there are other means, where the image signals are readily converted to digital signals by an A/D convertor or the like, and only the outlines of the defect portion is extracted by edge processing and so on, but there is no definition to the method of defect extraction under the present invention, and can be practiced by any method of extraction so that explanations shall proceed as based on the above mentioned example of the slice level method.

Upon returning to FIG. 1, the method of the present invention and the accompanying function will be explained. A step 1, by using a solid state video camera as an example, an adequate lighting is irradiated upon the inspected object and then the light passed through or reflected on the object is received.

At step 2, the image of the object is picked up by the video camera and an image signal is generated from the video camera. At step 3, the image signal is level-sliced by a preset threshold value at step 3A to thereby extract the portion that is assumed to be a flaw which is different in level. In this case, in the video camera, the horizontal scanning from a left upper pixel Ao of the image screen A is repeated and finished at the right lower pixel An at which the scanning of one field is ended.

Nextly, in order to modify the extracted signal to a form which can be easily stored in the memory, a binary signal conversion process therefor is conducted at step 4. In other words, the signal at the pixel portion which exceeds the threshold value may be made as a high level (or "1"), while the signal that is under the threshold level may be as a low level ("0"). The position of the binary coded extracted signal is stored in the memory at step 5. In this case, rather than simply storing the extracted signal in the memory, it should be stored in the memory as a position signal that indicates the position of the extracted signal within the image screen A.

At step 6, the position of the extracted signal that is stored in the memory (pixel position) is searched.

At step 7, from among the extracted signals that are searched in step 6, those at specific positions are selected. At this selection, as a condition of selection, based on the position of the extracted signal that was first detected, a threshold value is preset at step 7A so that a selection to the extracted signal position at how far away in the horizontal direction as well as the vertical direction from the base position would be the next base position setup is determined. In other words, based on the first detected extract signal position, it is to select up to how many extracted signals at pixels in the horizontal and vertical directions therefrom for the setup. Needless to say, the threshold values for the horizontal as well as vertical directions may be setup with different values, by which accommodation for wide long or vertical long defects is available.

Next, the selection conditions shall be explained in reference with FIG. 3. For explanation purposes, FIG. 2 illustrates a temporary setup shape for flaw P. When the image signal from the video camera that picks the flaw P up is processed by such aforementioned electronic processing and that felt to be a flaw is extracted while the image screen is divisioned into a lattice condition to illustrate the respective picture elements. Then, when the extracted signals (equal the "1" portion in the above) positions are shown on the latticed screen, it becomes as shown in FIG. 3. In FIG. 3, among the thin lined pixels within the latticed screen, the thick line portions show the pixels that correspond to the portions from which the signals are extracted, whereas 20 pixels from (1)-(20) are the signal extracted portions.

Now in FIG. 3, it is taken that T as a figure show how many away in the vertical direction from the base position and Y as a figure shows how many away in the horizontal direction from the base position. For instance, the pixel (2) is at a vertical distance "0" (T:0) apart from the pixel (1) at the base position that was first setup, and a horizontal distance apart is "1" (Y:1). In the same manner, by setting the pixel (2) position as the next base position, the pixel (3) will be (T:1) and (Y:1) against the pixel (2) in relative position. The relative positions up to the pixel (20) in the same manner are shown on FIG. 3.

As a condition of the signal selection at step 7, the setup of a threshold value for the condition is setup at step 7A, in other words, the tolerable vertical and horizontal distances (positions) from the base position are preset as the condition for the signal selection. For instance, if the selection condition is set at (T:1) and (Y:4), the extracted signals as shown on FIG. 3 shall all be consecutively selected as base positions so that the judgement that they are a part of one flaw is granted.

Assuming that the selection condition was (T:1) and (Y:3) as an example, the pixel (11) will not be selected as the based for the pixel (10) position, so that an upper portion Pl and a lower portion P2 of the flaw P shall be judged that there are two separate flaws. Further, in the case that there exists signals that do not satisfy the conditions, the signal selection processing is ceased at such point and proceeds to step 8.

Next, the signal position that was selected at step 8 is memorized in the memory. The position of such memorized signal is measured at step 9 for maximum vertical and horizontal distances. With the extracted signal selection condition same to the above as (T:1) and (Y:4), with the judgement as one single flaw, the maximum distance between extracted signals shall be vertical:6 and horizontal:6.

Step 10 is a step where an overall judgement process is conducted. In this case, some kinds of the size of flaws are determined on the basis of the above mentioned maximum distances between the extracted signals, and then data that indicate the sizes of the flaws are outputted or otherwise, the maximum vertical and horizontal distances between the extracted signals are predetermined and when there is a value that exceeds either one of the maximum distances, a signal that indicates that it is a defect that should be construed as flaw is outputted, etc. That is, a variation of judgement methods can be setup in compliance with the flaw detection purposes.

In other words, in the case that the selection condition is set as (T:1) and (Y:4) on the flaw P as shown on FIG. 2, bases on the above mentioned maximum distances of vertical:6 and horizontal:6, there would be a judgement that there is one flaw of specific size. Further, it is needless to say that different values for the vertical and horizontal aspects may be set. As such, judgement on the variation of flaw sizes will be available.

On the other hand, in the case that the selection condition is set as, for example, (T:1) and (Y:3), there is a case that a plural number of flaws that are assumed to be defects exist within the visual field that the camera picks up. In order to accommodate such case, steps 6–8 for position search, signal selection and memorizing process of the selected signals are repeated for several times. Here, in the case of signal selection at step 7, the selection is made by negating the previously selected positions of the extracted signals. After repetition of such functions, the maximum distances between the plural selected and extracted signals are measured at step 9. Otherwise, it can be that the maximum distances between the extracted signals be measured first, prior to entering the aforementioned process repetition.

Accordingly, when the above mentioned selection condition of (T:1) and (Y:3) is applied to the flaw P as shown on FIG. 2, by such processing, the data of two flaws with maximum distances as vertical 3 and horizontal 5 as well as vertical 3 and horizontal 5 are attained. And then, an overall judgement can be conducted on these flaws at step 10.

According to the present invention as above described, upon detection of various types of flaws, there is the effect that the setup of judgement basis against the flaw shapes and judgement of the flaw sizes can be easily and accurately conducted.

Further, since the processing method is constructed by very simple logics, the device manufacturing thereof is also easy.

Generally, such above described functions at electronic processors are carried out in electronic processing fashion by the computer utilization, but it is needless to say that the software making by operating the computer in order to conduct the principles of the present invention are exercised would be a very easy task for concerns involved in this business.

According to the present invention as above described, upon detecting flaws that vary in type, the setup of judgement basis for flaw shapes or judgement for the size determination, there is the merit that easy and accurate conduction is possible.

It should be understood that the above description is presented by way of example of the preferred embodiments of the invention and it will be apparent that many modifications and variations there of could be effected by one with ordinary skill in the art without departing from the spirit and scope of the novel concepts of the invention so that the scope of the invention should be determined only by the appended claims.

I claim as my invention

1. A method for judging defects in objects in which an image of an inspected object is picked up by a video camera, and the image signal from said video camera is divided into a matrix of horizontal and vertical lattice-like zones, and the brightness of said zones is sensed to detect the existence of a flaw, comprising:
    a) scanning said matrix from zone to zone;
    b) storing as a first base position the zone in first said matrix in which a defect is first detected;
    c) determining the second zone in which a defect is detected and the vertical and horizontal distance of said second zone from said first base position;
    d) selecting and storing the position of said second zone as a second base position wherein said horizontal and vertical distances are within preset distances;
    (e) thereafter determining the third zone in which a defect is detected and measuring the horizontal and vertical distance of said third zone from said second base position;
    (f) selecting and storing the position of said third zone as a third base position when said vertical and horizontal distances are within a preset distance; and
    (g) and thereafter judging the size of the defect based upon maximum distance in vertical and horizontal distances of the plurality of zones stored.

2. The method as claimed in claim 1, including the steps of sequentially determining each of the subsequent zones in which a defect is detected, measuring the horizontal and vertical distances of each of said subsequent zones from the zone having a defect immediately preceding in the scan and storing the position of each of said zones as base positions for measuring the location of the next succeeding zone having a defect.

3. The method as claimed in claim 1, wherein the preset distance upon which storage of the zone selected is variable.

4. The method as claimed in claim 1, wherein the preset distance upon which storage of the selected zone is made is set with respectively different values in the horizontal and vertical directions.

5. The method as claimed in claim 1, wherein when the maximum distances of the plurality of zones in the horizontal and vertical directions exceed a preset value, a judgement is made that such flaw is a defect.

* * * * *